(12) United States Patent
Hunter et al.

(10) Patent No.: US 10,012,609 B2
(45) Date of Patent: Jul. 3, 2018

(54) PACKETS FOR TESTING CHARGE STORAGE DEVICES

(71) Applicant: Nucleus Scientific, Inc., Cambridge, MA (US)

(72) Inventors: Ian W. Hunter, Lincoln, MA (US); Grant W. Kristofek, Wayland, MA (US); Dean Ljubicic, Somerville, MA (US)

(73) Assignee: Nucleus Scientific Inc., Cambridge, MA (US)

( * ) Notice: Subject to any disclaimer, the term of this patent is extended or adjusted under 35 U.S.C. 154(b) by 344 days.

(21) Appl. No.: 14/808,013

(22) Filed: Jul. 24, 2015

(65) Prior Publication Data

US 2016/0025668 A1    Jan. 28, 2016

Related U.S. Application Data

(60) Provisional application No. 62/028,421, filed on Jul. 24, 2014.

(51) Int. Cl.
| | | |
|---|---|---|
| *G01N 27/416* | (2006.01) | |
| *G01N 27/27* | (2006.01) | |
| *G01R 31/36* | (2006.01) | |
| *G01R 1/04* | (2006.01) | |
| *G01R 31/01* | (2006.01) | |

(52) U.S. Cl.
CPC ........... *G01N 27/27* (2013.01); *G01R 1/0408* (2013.01); *G01R 31/016* (2013.01); *G01R 31/3641* (2013.01)

(58) Field of Classification Search
CPC ..................................................... G01N 27/27

USPC .......................................................... 324/426
See application file for complete search history.

(56) References Cited

U.S. PATENT DOCUMENTS

| | | | | |
|---|---|---|---|---|
| 2,390,784 | A | * 12/1945 | Drobish | ............... G01R 31/016 29/25.42 |
| 3,930,993 | A | * 1/1976 | Best | ........................ B07C 5/344 209/551 |
| 3,979,671 | A | 9/1976 | Meeker et al. | |
| 5,065,106 | A | 11/1991 | Hendrick | |
| 5,113,133 | A | 5/1992 | Conti et al. | |
| 5,214,389 | A | 5/1993 | Cao et al. | |
| 5,583,446 | A | 12/1996 | Takeuchi et al. | |
| 5,635,848 | A | 6/1997 | Hammond et al. | |
| 6,184,688 | B1 | * 2/2001 | Kamitani | ............. G01R 31/016 324/519 |

(Continued)

*Primary Examiner* — Richard V Muralidar
(74) *Attorney, Agent, or Firm* — Occhiuti & Rohlicek LLP (57) ABSTRACT

A sachet includes a first wing made of a flexible material and having a first perimeter region circumscribing a first central region; a second wing made of the flexible material; a hinge connecting the first and second wings along a common boundary; an adhesive material applied to the perimeter region on the first wing; a first electrically conducting electrode formed on the first wing within the central region of the perimeter region; a second electrically conducting electrode formed on the second wing in a region that is opposed to and in alignment with the first contact area on the first wing; an array of contact pads formed on at least one of the first and second wings; first and second conducting traces electrically connecting first and second groups of one or more contact pads among the array of contact pads to the first and second electrodes, respectively.

12 Claims, 6 Drawing Sheets

(56) References Cited

U.S. PATENT DOCUMENTS

| | | | |
|---|---|---|---|
| 6,344,751 B1 | 2/2002 | Prokopp et al. | |
| 6,820,472 B2* | 11/2004 | Ranchin | G01M 13/025 |
| | | | 73/115.02 |
| 8,736,273 B2* | 5/2014 | Stancu | G01R 31/3627 |
| | | | 324/425 |
| 9,714,983 B2* | 7/2017 | Hunter | G01R 31/3675 |
| 2003/0085723 A1 | 5/2003 | Martens et al. | |
| 2007/0286429 A1* | 12/2007 | Grafenberg | H04R 25/30 |
| | | | 381/60 |
| 2013/0323864 A1 | 12/2013 | Mo et al. | |

* cited by examiner

PACKETS FOR TESTING CHARGE STORAGE DEVICES

This application claims the benefit under 35 U.S.C. § 119(e) of Provisional Application Ser. No. 62/028,421 filed Jul. 24, 2014, entitled "Instrumented Packets for Testing Charge Storage Devices," the entire contents of which are incorporated herein by reference.

TECHNICAL FIELD

This invention generally relates to test instruments and related equipment for measuring and for electrically and mechanically characterizing test devices such as actuators, batteries, capacitors, supercapacitors, ultracapacitors, hybrid capacitors, pseudocapacitors, biological samples, dielectrics, gels, liquids, solids, etc.

BACKGROUND

The development of high energy density storage devices can be a laborious and time consuming process. A typical energy storage device might include a first polymer electrode, a second electrode in electrochemical communication with the first electrode, a separator material between the two electrodes, and an electrolyte or other mobile phase in contact with both electrodes that can dissociate into anions and cations. There are many different chemical materials that could be used for each of these elements. So, the number of possible of combinations that might need to be tested can be huge. For testing these combinations one has to, in essence, build a representative device for each combination of materials and then run that device through the desired set of tests to characterize that combination of materials. Thus, finding the best combination of materials can involve constructing and electrically testing thousands and thousands of devices representing the many different possible combinations of materials and electrolytes.

The regimen of tests required to satisfactorily measure the electrical characteristics of a device might also be quite large. For example, the tests might include measuring capacitance, resistance, energy in versus energy out, Coulombic efficiency, energy density, power density, specific energy, specific power, IR drop, IR gain, current density, etc.

SUMMARY

The embodiments described here, particularly when used in combination with each other, provide a rapid, efficient, consistent, and reliable way of testing test devices.

In general, in one aspect, the invention features a sachet including: a first wing made of a flexible material, the first wing having a first perimeter region circumscribing a first central region; a second wing made of the flexible material; a hinge connecting the first and second wings along a common boundary; an adhesive material applied to the perimeter region on the first wing; a first electrically conducting electrode formed on the first wing within the central region of the perimeter region; a second electrically conducting electrode formed on the second wing in a region that is opposed to and in alignment with the first contact area on the first wing; an array of contact pads formed on at least one of the first and second wings; a first conducting trace electrically connecting a first group of one or more contact pads among the array of contact pads to the first electrode; and a second conducting trace electrically connecting a second group of one or more contact pads among the array of contact pads to the second electrode.

Preferred embodiments includes one or more of the following features or aspects. The hinge is made of flexible material with a row of perforations formed therein. The second wing has a second perimeter region circumscribing a second central region and further including the adhesive material applied to the second perimeter region on the second wing. The sachet further includes a third conducting trace connecting one of the contact pads in the array of contact pads to the first electrode, the third conducting trace being separate from the first conducting trace. The sachet also includes a fourth conducting trace connecting one of the contact pads in the array of contact pads to the second electrode, the fourth conducting trace being separate from the second conducting trace. The first perimeter region is separated from the central region to form a first intermediate region circumscribing the first central region, and the sachet also includes: a first prewired contact pad located in the first intermediate region; and a conducting trace electrically connecting one of the contact pads of the array of contact pads to the first prewired contact pad.

There is a wide variety of sample cell types that may be constructed and tested with the sachet described herein including, for example, actuators, batteries, capacitors, supercapacitors, ultracapacitors, pseudocapacitors, hybrid capacitors, biological samples, dielectrics, gels, liquids, solids, etc. In addition, the use of the sachet is not limited strictly to testing active elements (e.g. batteries or capacitors); it is also possible to use the sachet to test passive elements (e.g. resistive films). Indeed, one can use it to precisely test any device for which a voltage/current may be measured under pressure loading. Furthermore, the sachet may also be used to precisely monitor creep or expansion as a function of pressure, temperature, time, voltage, current and to evaluate the stiffness of samples as function of pressure, temperature, time, voltage, current.

Other advantages of the sachet described herein are that samples may be constructed in fully environmentally sealed sachet, allowing for contaminant-free electrochemical testing; environmentally sensitive samples may be constructed in an oxygen free environment (e.g. glove box) and then removed for testing outside of glove box; low manufacturing cost of sachet allows for creation of individual "disposable" samples and/or long-term storage for archival purposes, future testing, etc.; and samples can be marked and stored for archival or cataloging purposes;

DESCRIPTION

The testing system described herein includes a test instrument 100 (shown in FIG. 1) and a specially designed sample holder or sachet 500 (shown in FIG. 6) which fits into test instrument 100 and holds the different electrochemical materials the electrical properties of which are to be tested.

The Test Instrument

Figure 1:
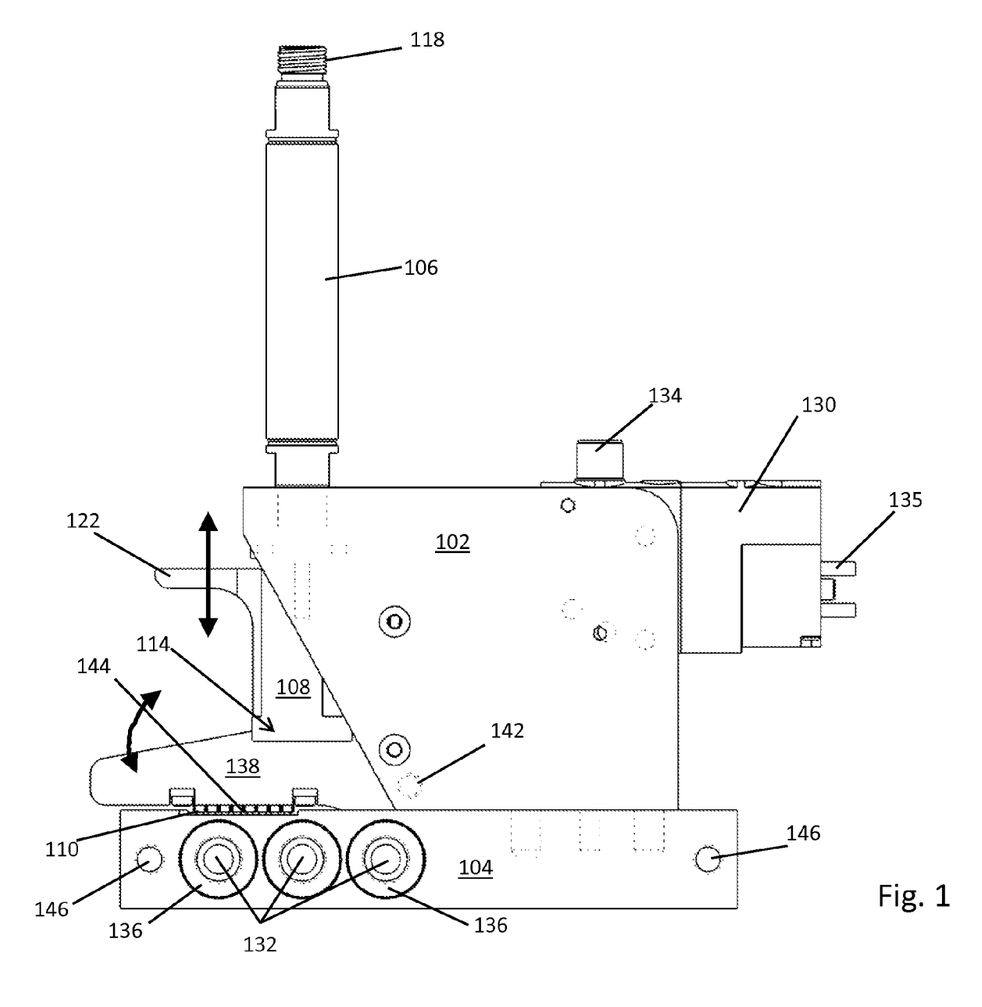
FIG. 1 shows the left side of a test instrument.

Referring to FIG. 1, test instrument 100 is capable of controlling the pressure that is applied to the sample and the temperature of the sample during measurement of its electrical characteristics. It is capable of measuring the physical expansion of the test sample as it is being maintained under a constant pressure while its electrical characteristics are being measured. It is capable of controlling the temperature of the test sample during those measurements. And it is capable of measuring the pressure generated by the test sample as its thickness is constrained to a constant value during electrical testing.

Test instrument 100 includes a machined aluminum body 102 mounted on a machined aluminum support platform 104. Body 102 provides support for a linear actuator 106 which controls the up and down movement of a probe head 108 attached to the working end of actuator 106. Actuator 106 is screwed into the top side of body 102 with its actuator shaft 112 extending down towards support platform 104. Probe head 108 is screwed onto the end of actuator shaft 112 and has a flat working surface 114 on its lowermost end which contacts the test sample (not shown) during operation. Actuator 106 is used to apply a controlled force/pressure to a sample (not shown) which is positioned in a flat recessed area 110 on supporting platform 104 during testing. Care is taken to make sure that the longitudinal axis of actuator 106 is perpendicular to the plane of recessed area 110 and that working surface 114 of probe head 108 when assembled onto the working end of actuator 106 is parallel to the flat surface of recessed area 110. This is to assure that the force/pressure that is applied to the test sample is uniform across the contacted area of the sample.

In the described embodiment, the linear actuator is an Airpel Anti-Stiction® Air Bearing cylinder from Airpot Corporation. It is a pneumatic actuator capable of highly accurate force control due to its low stiction. It includes a graphite piston and a borosilicate glass cylinder with an air bearing between the piston and the glass cylinder. It is capable of responding to forces as low as only a few grams and pressures less than 0.2 psi. The force that is applied by the air cylinder is a known function of the pressure of the air supplied to the cylinder. So, by monitoring the air pressure with an inline pressure, analog output sensor, one can easily determine the force/pressure that the probe head applies to the test sample.

Other types of actuators could also be used, such as for example, electromagnetic Lorentz-force actuators of the type described in U.S. Pat. No. 7,833,189, entitled "Controlled Needle-Free Transport", incorporated herein by reference. It is generally desirable, however, to use those types of actuators having low stiction given the sensitivity of the tests that likely will need to be performed. Use of precision air-bearing cylinder has advantages over many of the alternatives. It minimizes the frictional forces typically associated with the traditional linear elements. The reduced friction, in turn, maximizes the accuracy of the thickness measurement and optimizes the dynamic range and sensitivity of the device. Also, long duration tests benefit from the use of pneumatic actuators, as they do not typically require constant energy input (i.e., power) to achieve consistent and uniform force application. Short duration tests with high bandwidth or large dynamic range may benefit from Lorentz force actuators.

If an actuator other than the one described herein is used, the test instrument will also need to include a separate force sensing device optionally located between the probe head and the actuator shaft.

Figure 2:
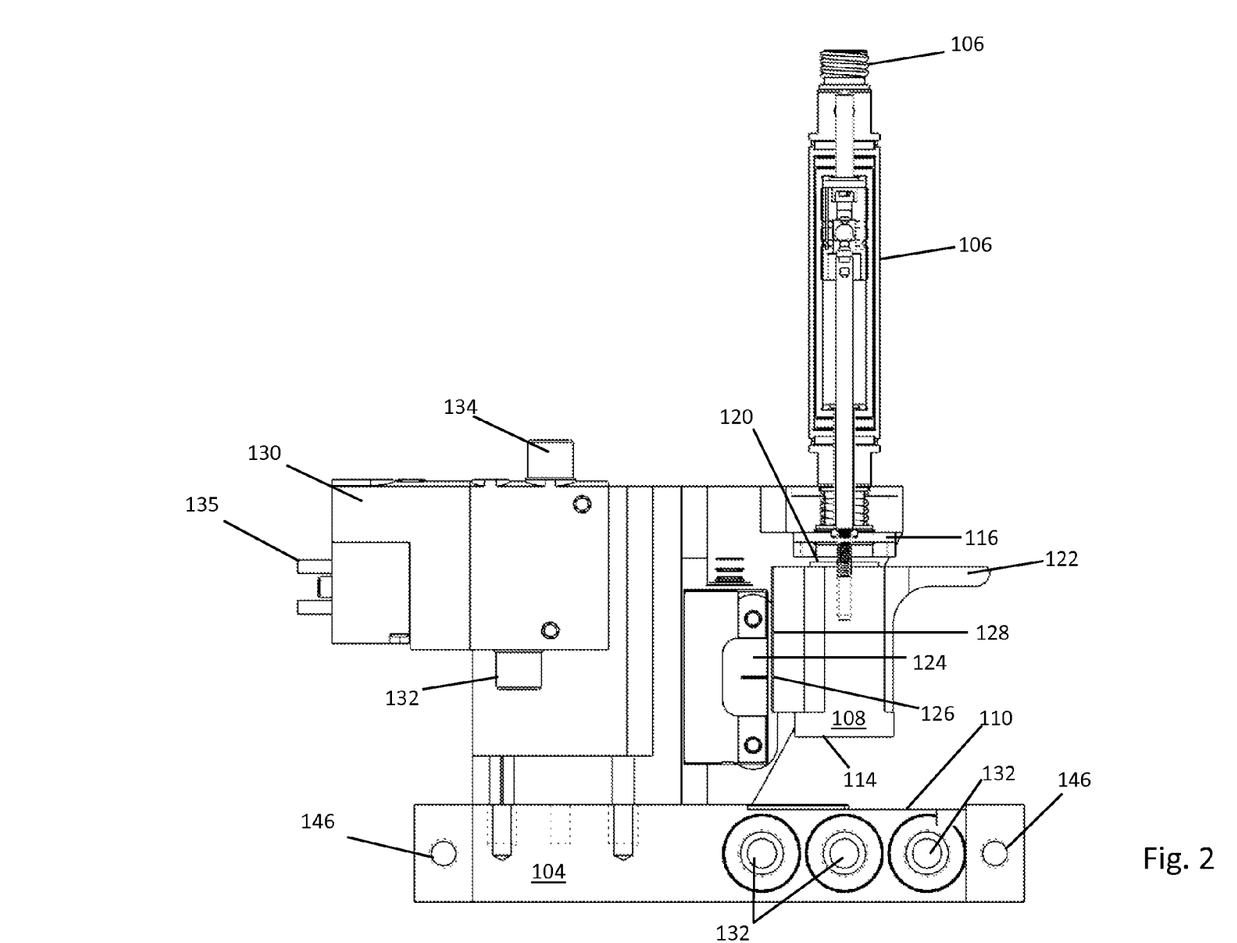
FIG. 2 shows in a partial cross-section the test instrument of FIG. 1 from the right side.

As shown in FIG. 2, a secondary air bearing support element 116 is located at the output end of actuator 106. This provides off axis stiffness for shaft 112 with little to no stiction to keep shaft 112 precisely aligned perpendicular to the plane of recessed area 110. At the top of actuator 106 is an input port through which pressurized air is supplied to actuator 106. This input port has a threaded portion onto which the fitting on the supply line (not shown) is threaded.

Probe head 108 includes a magnetic ring 120 on its upper surface encircling actuator shaft 112 where it is screwed into the top of probe head 108. Also, probe head 108 includes a lift arm 122 located and extending away from its top front region. Lift arm 122 provides an easy way for the operator of test instrument 100 to manually lift probe head 108 when it is necessary to ether insert a new test sample into recessed area 110 or remove a test sample from recessed area 110 pr manually lower probe head 108 after a test sample has been inserted. Ring magnet 120 holds probe head 108 in its up position while these operations are being performed.

Test instrument 100 also includes an optical sensor assembly 124 mounted on body 102 at the back of and close to probe head 108. Optical sensor assembly 124 includes a read head sensor 126 which detects the markings on a scale 128 that is mounted on the back of probe head 108. In the described embodiment, optical sensor assembly 124 is a TONiC™ made by Renishaw. It is a super-compact, non-contact optical encoder that offers speeds up to 10 m/s and resolutions down to 1 nm.

By detecting movement of scale 128 which is mounted on probe head 108, optical sensor assembly 124 provides a way to accurately measure the absolute position of probe head 108 when performing measurements on the test sample. Thus, if the sample swells when power is being delivered to the test sample or when it is being discharged, the precise amount of the swelling can be measured using optical sensor assembly 124. In addition, with the aid of a controller, the pressure being applied by the probe head to the sample can be varied so as to constrain the thickness of the test sample to a constant maximum value.

Alternative sensors other than optical sensors could also be used, including for example, capacitive probe sensors and magnetic position sensors.

Mounted on the back of body 102 is a solenoid 130 which, under external control, turns on and off the supply of air pressure to actuator 106. It has an input port 132 to which an air supply line (not shown) is connected, an output port 134 to which a line (not shown) connected to input port 118 of actuator 106 is attached, and a power input 135 for operating the solenoid.

Figure 4:
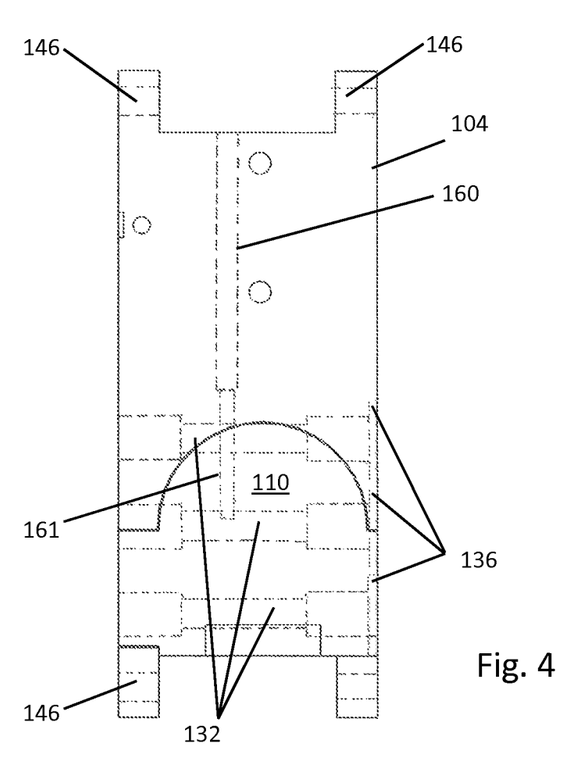
FIG. 4 shows a platform which is part of the test instrument shown in FIG. 1.

Referring to FIGS. 1 and 4, for purposes of temperature control, platform 104 has three flow channels 132 extending from one side to the other directly beneath recessed area 110 into which test samples are inserted for testing. At each end of each flow channel 132 is a threaded portion 134 which allows a threaded fitting (not shown) to be screwed into the platform. On one side of platform 104, there is a recessed area 136 circumscribing the opening to each channel 132. These recessed areas 134 are for receiving O'ring seals (not shown). During operation of the test instrument, heated or cooled water is flowed through these channels 132 to control the temperature of platform 104 and thereby controlling the temperature of the device resting on the platform.

Figure 3A:
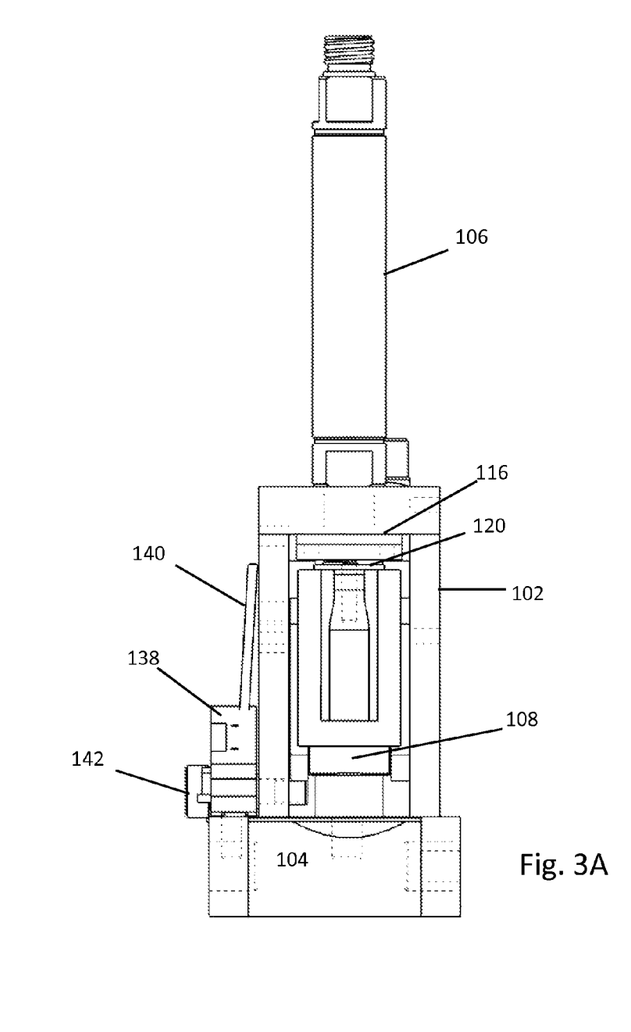
FIGS. 3A and B show front of the test instrument of FIG. 1, one in partial cross-section to more clearly reveal relevant internal features.
Figure 3B:
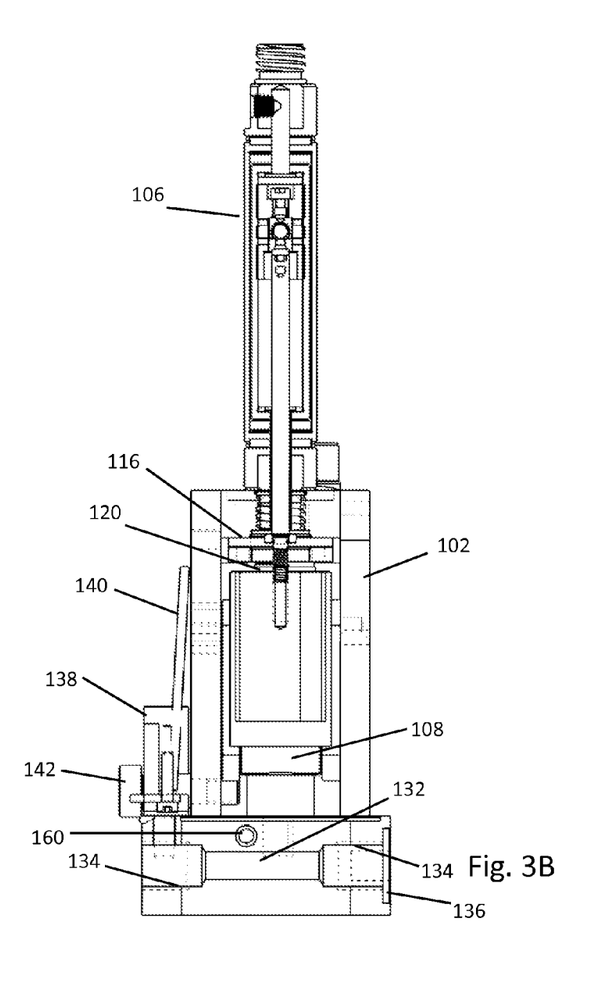

Referring to FIGS. 3B and 4, platform 104 includes a channel 160 drilled in through the back and extending to a location that is between the middle flow channel 132 and the middle of recessed area 110. A temperature sensing device 161 (e.g. thermistor, resistance temperature detectors, thermo pile/IR—non contact) is positioned within channel 160 at the location below recessed area 110. This device is used for temperature sensing and control.

The design of the test instrument with particular regard to the heating and cooling manifold assembly just described enables it to be operated as a standalone unit or ganged together with any number of other test instruments. Depending on how the test instrument is setup (i.e., either as a standalone or ganged together with other test instruments) appropriate fittings are screwed into the threaded areas at the ends of flow channels 132. If the test instrument is set up as a standalone unit, then fittings for making connections to the water lines of the temperature control system are screwed into the threaded portions 134.

If the test instrument is set up as part of an array, they are lined up next to each other so that their sides abut and the flow channels are in alignment with each other. In this configuration, O-rings are inserted into the recessed areas 136 around the flow channels 132. When one unit abuts up against a neighboring unit, the O-ring contacts the side wall of the platform of the neighboring unit and forms a seal which prevents fluid from leaking out of the manifold. The multiple units are then held together by rods (not shown) with threaded ends that are inserted in the aligned holes 146 (see FIG. 1) of the multiple test instruments in the lineup. Nuts at the end of those threaded rods are tightened down to force the units tightly together so the O-rings form good seals in the flow channels at the interfaces between neighboring units. In this way, it is possible to set up large clusters of test instruments for massively parallel testing of devices thereby enabling more rapid prototyping and experimentation on complex composite systems. Also, individual test devices can be easily added and removed.

As an alternative to the heating/cooling manifold described above, one could instead use individual heating elements (e.g. Peltier devices or resistive heaters) that are mounted in recessed areas 110 on platform 104. If that approach is used, it would be appropriate to place insulators between the heater elements and the platform to reduce the loss of heat to the more thermally conductive platform. In addition, temperature sensors would also be placed above the heater elements to accurately monitor the temperature of the test device. By using the individual heaters the speed at which the device temperature can be changed is much higher as compared to the manifold approach in which the temperature of the water and the platforms (representing a much higher thermal mass) needs to be changed.

For making electrical contacts to test samples in the test instrument, there is a contactor assembly 138 mounted on one side of body 102. Contactor assembly 138 includes a 2×8 array of POGO LC contactors 144 attached to its bottom side. The pattern and spacing of the contactors is identical to the pattern and spacing of the contact pads on the test sample, which is described in greater detail below. A bolt 142 which screws into body 102 at location 144 (see FIG. 3) provides a shaft about which contactor assembly 138 can be pivoted to raise and lower the contactors. Extending upward from the contactor assembly is a lever arm 140 which the operator uses to manually rotate the unit about the pivot established by bolt 142 to thereby raise and lower the contactors. The pogo pins are appropriately preloaded by torsion springs so as to establish good contact with the contact pads when the contactor assembly is lowered into position.

Figure 5:
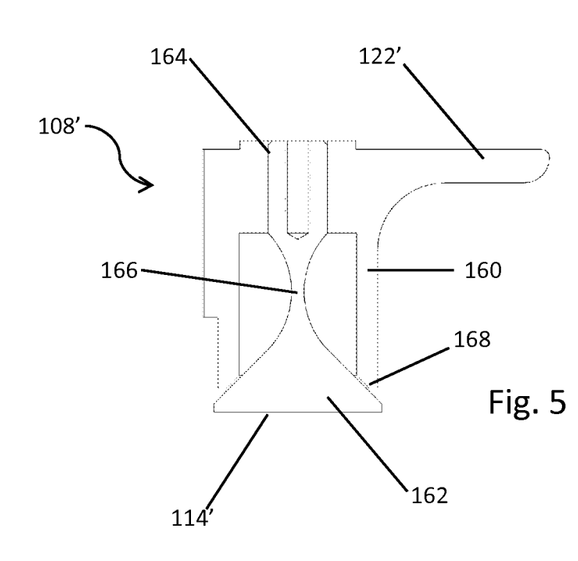
FIG. 5 shows an alternative probe head design.

An alternatively designed probe head 108' is shown in FIG. 5. It has the advantage of having a contacting surface 114' that can easily tilt by a small amount in any direction to thereby accommodate a sample that might not have a parallel top surface. This tilting ability assures a more uniform distribution of the applied pressure over the surface of the test sample.

The alternative probe head 108' includes a housing 160 which encloses a contactor probe 162 having a bottom surface 114' that contacts the sample under test. Housing 160 has a hollow region in which contactor probe 162 is largely contained except for a small portion of the bottom portion of contactor probe 162 that extends outside of the housing (this is the portion that contacts the test sample). At its upper end, there is a hole that accommodates to top end of contactor probe 162. The bottom surface 114' of contactor probe 162 is flat and circular. The upper end 164 of contactor probe 162 is cylindrically shaped and fits into the hole in housing 160. Between the flat bottom surface and the cylindrically shaped upper end, the contactor probe is conically shaped and tapers down to a narrow diameter neck and then tapers back out to the diameter of the cylindrically-shaped upper end thereby forming a rigid conical flexure region. The opening in housing 160 into which contactor probe fits is cylindrical, has a slightly smaller inside diameter than the diameter of the flat circular surface of probe head 108', and has a beveled edge 168 which has the same angle as the angle of the tapered portion of the probe head to which it is adjacent. Narrow conical flexure region 166 is sufficiently thin so as to enable the head to easily flex and thereby permit the probe head to tilt off axis by a sufficient amount to accommodate any slight tilt in the top of the sample under test. The diameter of the narrowest portion is, however, designed to be large enough to enable the probe head to transmit the maximum force desired for testing the sample without buckling or deforming.

The Sachet

Figure 6:
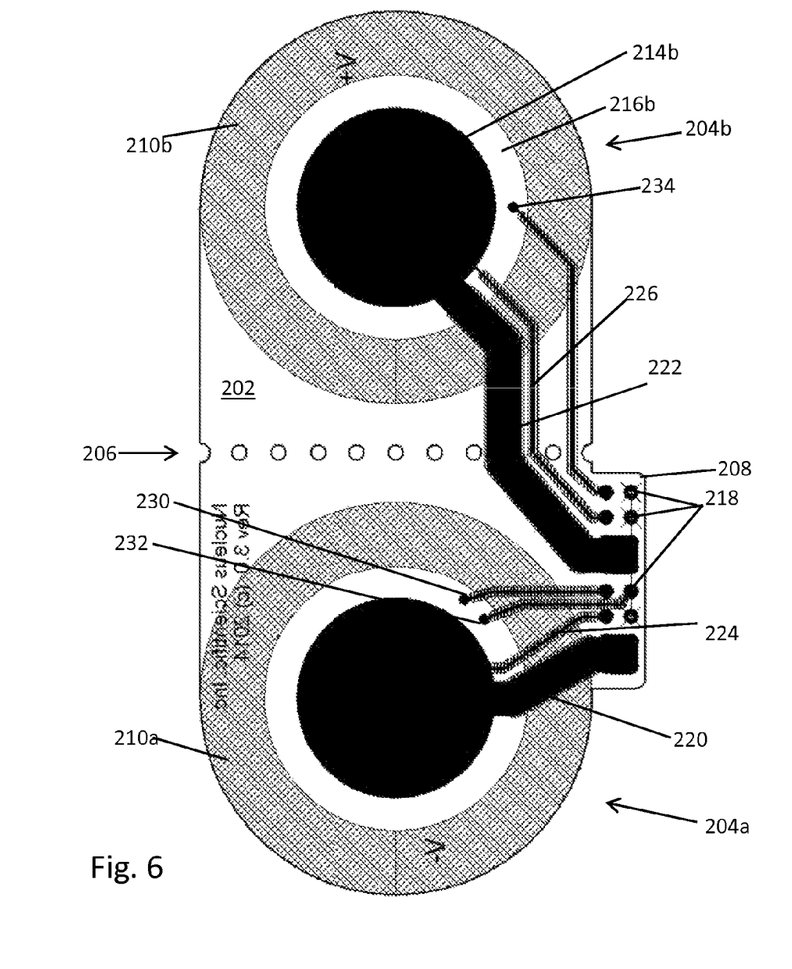
FIG. 6 shows a sachet in its fully open position.
Figure 7:
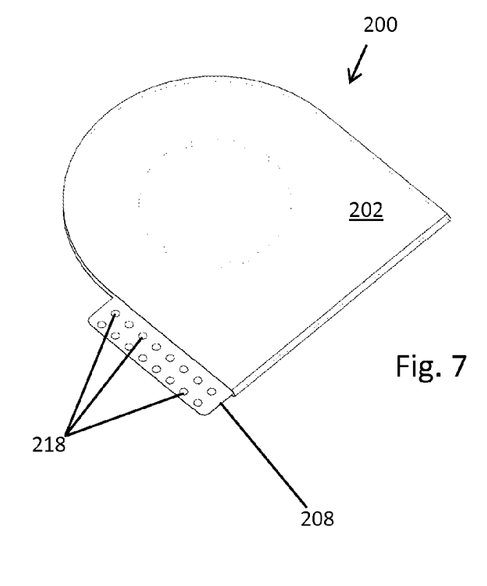
FIG. 7 shows the sachet of FIG. 6 in a closed configuration.

Referring to FIG. 6, sachet or sample holder 200 is a structure that enables one to easily assemble a cell for testing the performance of a particular device chemistry. The materials to be tested are placed onto sample holder 500, it is folded together to form a sealed packet or cell as shown in FIG. 7, and that sealed packet is placed on the test instrument to perform an array of electrical tests.

Sample holder 200 is constructed from a flexible, highly impermeable, hydrophobic sachet material 202 (Kapton a.k.a. polyimide, or PET/mylar) which allows for dynamic motion of the materials under test within while preventing contamination by external environmental elements. It has two symmetrical portions or wings 204a and 204b which are separated by a hinge 206. In the described embodiment, hinge 206 is formed by a linear sequence of small holes or perforations through film 202 which renders the film more easily foldable along the line defined by the perforations. Except for a contact pad tab 208 on one of the wings, wings 204a and 204b of sample holder 200 have the same shape and size so that when they are folded over onto each other, they align and match up with each other.

In the illustrated embodiment, the outer perimeter of each wing 204a and 204b is in the shape of a "U" with parallel opposite sides that join a curved portion that represents the bottom of the "U". The outer perimeter of the curved portion is a segment of a circle. Note that the shape and size of recessed area 110 in platform 104 of the test instrument (see FIG. 4) is the same as that of the assembled sachet so as to hold the sachet in a precise and repeatable location for testing with the tab properly aligned with the contactor assembly. Of course, other shapes for the sachet are also possible which accomplish the same objective.

On each wing 204a and 204b there is an annular region 210a and 210b that completely circumscribes a central region and the outer perimeter of which coincides with the curved outer perimeter of the wing. The annular regions 204a and 204b are arranged and sized so that they completely align and match up with each other when film 202 is folded together about hinge 206. Applied to the entire annular region on each wing is a pressure sensitive adhesive (PSA) covered by ring of release material 212. In the described embodiment, the contact adhesive is acrylic-based 3M 467MP pressure sensitive adhesive. The ring of release material paper renders the test sample more easy to handle during assembly and prevents any foreign objects from inadvertently sticking to the adhesive.

Alternative sealing methods can, of course, be used. For example, heat sealing through ultrasonic welding is one possibility. Or other types of glue can be used. The choice may depend somewhat on the materials that will be tested within the sachet and the need for rapid assembly and the degree to which sachet must be environmentally sealed.

Within the center of each annular region 210a and 210b are large circular contact electrodes 214a and 214b that are coaxially aligned with the annular region. The contact electrodes 214a and 214b cover most of the center region inside the annular region except for a ring region 216a and 216b surrounding the contact pad and separating it from the annular region.

Tab 208 that extends off to the side of one of the wings 204a includes two parallel rows with eight contact pads 218 in each row. A wide conducting trace 220 connects four of the contact pads 218 to central contact electrode 214a and another wide conducting trace 222 connects four other contact pads 218 to central contact electrode 214b. In addition to the wide conducting traces 220 and 222, there are two narrow conducting traces 224 and 226, one connecting a contact pad 208 to electrode 214a and another connecting another contact pad 218 to electrode 214b. The wide conducting traces 220 and 222 are for supplying power to electrodes 214a and 214b, which is why those conducting traces are wide. Since they will carry larger currents, their resistances need to be low to avoid causing excessive voltage drops and heating between the contact pads 218 and the electrodes 214a and 214b. The narrow conducting traces 224 and 226 serve as sensing traces for measuring the voltages of the corresponding electrodes. Since they will carry very little current, there will be no appreciable voltage drop and they can therefore be narrower.

The unused contact pads, which equal six in number in the illustrated embodiment, can be used to connect to other embedded sensors within the device structure that one might wish to include. For that purpose, in the described example, two contact areas 230 and 232 are included in ring 216a and one contact area 234 is included in ring 216b. These contact areas are, in turn, connected to corresponding pads on tab 208 via electrically conducting traces. The contact areas in the open areas of the two rings 216a and 216b provide points to which other embedded sensors can be connected. By using such pre-wired reference electrode traces one can: attach various reference elements (e.g. silver, platinum, gold, copper, etc.); construct many varieties of sample types; and implement various electrochemical test protocols/procedures (e.g. cyclic voltammetry, galvanostatic measurement, potentiostatic measurement, impedance spectroscopy, etc.) using the same test apparatus, electronics, and sachet. For example, it is possible to measure sachet temperature by resistive measurement of a calibrated trace, in which case two of the contact pads 218 on tab 208 would be used to connect to the two ends of the calibrated trace.

When the assembled sachet, with the test material inside the sealed packet, is inserted into the test instrument, tab 208 and the contact pads 218 align with the contactors 144 on the contactor arm assembly 138 of the test instrument thereby allowing external test circuitry to communicate with the test device and any sensors that are incorporated into the test device.

In the described embodiment, the electrodes and leads are made electrolytic copper, plated with electroless nickel and then electroplated with a low resistance, low corrosion, low contamination, high purity soft-gold. The metal areas can be fabricated by using any of a number of different, well known techniques. For example, they can be fabricated by using ENIG (the Electroless Nickel Immersion Gold process). Or one could use soft gold electroplating. Both of those techniques involve a gold layer formed on a nickel layer.

Alternatively, the contacts could be fabricated from other metals such as aluminum. The choice of material may depend upon the chemistry of the materials that are to be put in the sachet for testing, some materials being more resistant to degradation and/or corrosion when exposed to a particular chemistry than others.

Assembly of the test sample is straightforward and simple. With wings 204 in their unfolded or open position, the release film is removed from the adhesive areas. Then, the materials to be tested are applied to one of the electrodes. When the device structure is fully assembled, one wing is folded about the fold line onto the other to form a sealed packet with the device contained inside. The use of the perforated fold line makes possible repeatable, rapid assembly of samples without having to use a special jig or procedure to align electrode pads.

The sachets can be designed with the objective of minimizing the compressive force exerted by the sealing ring on test sample material. For example, the compliance of the film, the distance from edge of the adhesive region to the electrode (or sample area), and the possibility of including a shim washer element between the adhesive area and the electrode are all design parameters or features that can be used to reduce or prevent undesirable non-planar distortion of the sample.

The process for fabricating the sachets uses conventional, commercially available techniques. In general, a stack of the different layers is assembled and bonded together. There is a first dielectric layer (e.g. a polyimde layer), followed by a layer of adhesive, then the layer of conducting traces, followed by another layer of adhesive, and ending with a final dielectric layer on top.

In the described embodiment, the sachet employs one ring of a contact adhesive on both wings to form the seal and hold the two wings together. Under some circumstances, however, this may not provide sufficient sealing, especially when exposed to certain electrolytes that might be used in the sample under test. A more secure and more permanent way of sealing the two wings together is to use two concentric rings of adhesive. The outer ring uses the adhesive material described above; while the inner ring uses an epoxy that takes time to cure perhaps with heat or UV. The outer ring holds the assembly together while the epoxy cures. The epoxy ring protects the adhesive from being exposed to the electrolyte and after it cures provides both a stronger bond holding the two wings together and one that is more resistant to degradation by the electrolytes and also evaporation and/or oxygen or other gas permeation.

Optionally, the sachet can also include a marking coating applied to the backside to provide an area on which the test operator can write identifying information and other relevant data relating to that particular test device.

Figure 8:
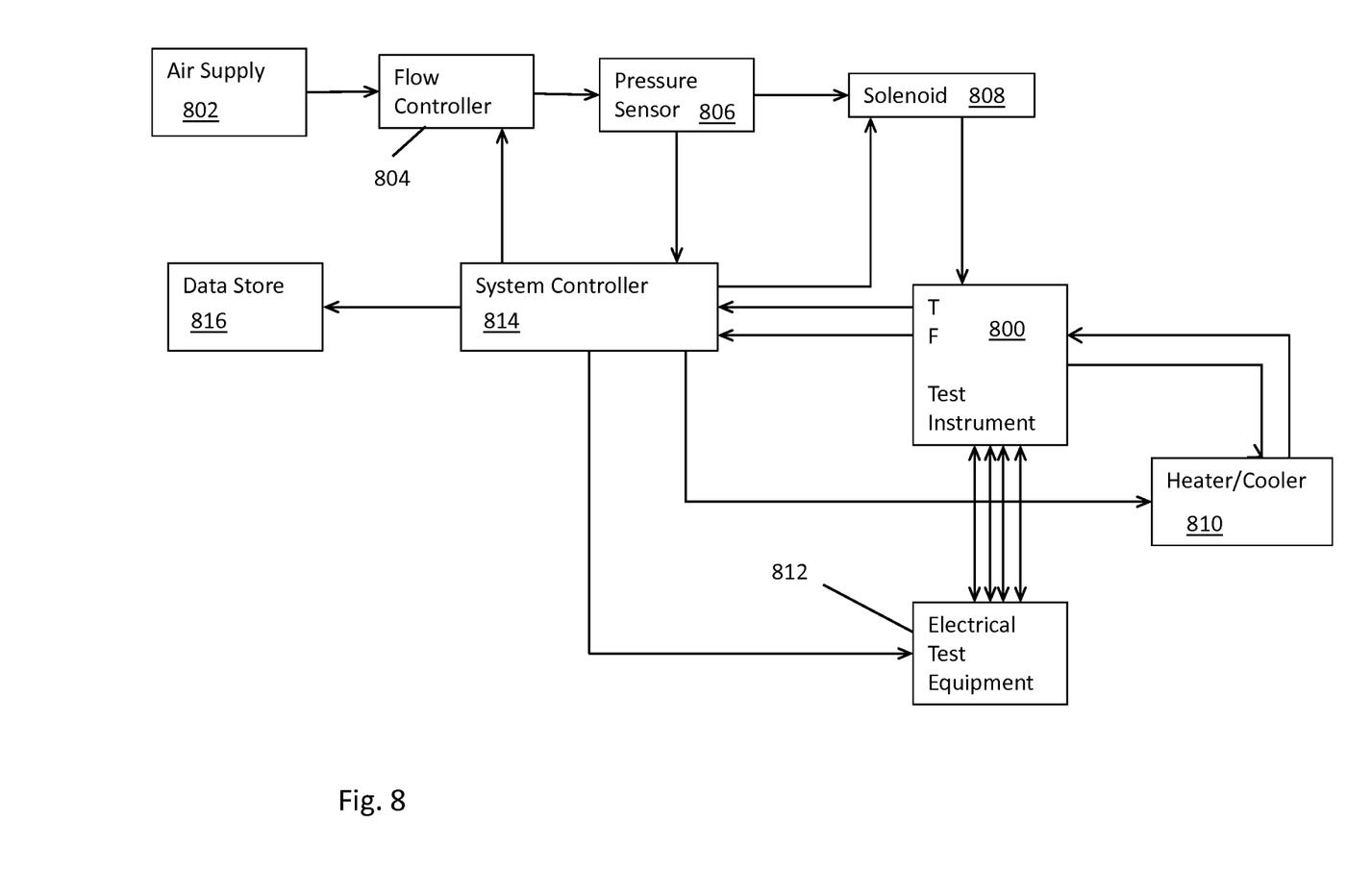
FIG. 8 is a block diagram of a test system including the test instrument described above.

Referring to FIG. 8, a complete system, including a test instrument 800 constructed in accordance with the ideas presented herein, includes an air supply 802 (or source of pressurized gas) for operating the air cylinder in test instrument 800, a flow controller 804 which modulates the flow of air to the air cylinder which in turn controls the force applied by that air cylinder to the test sample, a pressure sensor 806 for measuring the force that is applied by test instrument 800 to the test sample, and a solenoid 808 for turning on and off the flow of gas to the test instrument 800.

The system also includes a heating/cooling system 810 for controlling the temperature of the fluid (e.g. water) that is supplied to the test instrument platform on which the test sample is resting during testing.

To perform the desired electrical measurements, there is a rack of electrical test equipment 812. This includes at least a power supply for powering the device under test as well as other measurement instruments appropriate for the types of electrical measurements that are to be performed such as, for example, device capacitance, resistance, energy in/out, Coulombic efficiency, energy density, power density, specific energy, specific power, IR drop, IR gain, current density, etc. The electrical test equipment is electrically connected via wires to the contactor assembly which, in turn, provides the electrical connections to the device under test.

A system controller 814 controls the operation of flow controller 804, solenoid 808, heating/cooling system 810, and electrical test equipment 812. It runs the various tests, ether under the manual control of an operator or automatically under programmed control, and stores the acquired data along with the relevant operating conditions (e.g. temperature, pressure) in local memory 816.

Air supply 802, flow controller 804, pressure sensor 806, and solenoid 808 make up the force controller, i.e., the subsystem that sets and controls the force that is applied to the test sample by the probe head. If another type of actuator is used instead of an air cylinder as described herein other components would be substituted for these components. For example, if a Lorentz-force linear actuator is used, then a variable power supply (or current supply) is substituted for the air supply and flow controller. And the force measurement might be made by a strain gauge that is integrated into the probe assembly.

Other embodiments are within the following claims. For example, a microcontroller and memory chips can also be included on the sachet thereby allowing for the creation of an intelligent device that may, for instance, know its test history, its material construction, and even the use of the data to feed back for optimal experimental implementation in massively parallel test environment. Also, the sachet can include a septa for introducing and/or reintroducing fluid (e.g. electrolyte) into an already assembled test sample.

What is claimed is:

1. A sample holder comprising:
   a first wing having a first perimeter region circumscribing a first central region;
   a second wing;
   a hinge connecting the first and second wings along a common boundary;
   an adhesive material applied to the first perimeter region on the first wing;
   a first electrically conducting electrode formed on the first wing within the central region of the first perimeter region;
   a second electrically conducting electrode formed on the second wing in a region that is opposed to and in alignment with the first electrically conducting electrode on the first wing when the first and second wings are folded together about the hinge;
   an array of contact pads formed on at least one of the first and second wings;
   a first conducting trace electrically connecting a first group of one or more contact pads among the array of contact pads to the first electrode; and
   a second conducting trace electrically connecting a second group of one or more contact pads among the array of contact pads to the second electrode.

2. The sample holder of claim 1, wherein said second wing has a second perimeter region circumscribing a second central region and further comprising the adhesive material applied to the second perimeter region on the second wing.

3. The sample holder of claim 1, further comprising a third conducting trace connecting one of the contact pads in the array of contact pads to the first electrode, said third conducting trace being separate from the first conducting trace.

4. The sample holder of claim 3, further comprising a fourth conducting trace connecting one of the contact pads in the array of contact pads to the second electrode, said fourth conducting trace being separate from the second conducting trace.

5. The sample holder of claim 1, wherein the first perimeter region is separated from the central region to form a first intermediate region circumscribing the first central region, said sample holder further comprising:
   a first prewired contact pad located in the first intermediate region; and
   a conducting trace electrically connecting one of the contact pads of the array of contact pads to the first prewired contact pad.

6. The sample holder of claim 1, wherein the first wing and the second wing are made of a flexible material.

7. The sample holder of claim 6, wherein said flexible material comprises a polyimide.

8. The sample holder of claim 6, wherein said flexible material comprises a PET/mylar.

9. The sample holder of claim 6, wherein the hinge is made of said flexible material with a row of perforations formed therein.

10. The sample holder of claim 1, wherein the first wing, the second wing, and the hinge are a unitary structure.

11. The sample holder of claim 1, wherein each of the first conducting trace and the second conducting trace comprises gold.

12. The sample holder of claim 1, wherein each of the first conducting trace and the second conducting trace comprises a gold layer on a nickel layer on a copper layer.

* * * * *